United States Patent [19]

Nakashima

[11] Patent Number: 5,616,756
[45] Date of Patent: Apr. 1, 1997

[54] ORGANOSILICON COMPOUNDS AND METHOD FOR THE PREPARATION THEREOF

[75] Inventor: Hisataka Nakashima, Fukuoka Prefecture, Japan

[73] Assignee: Dow Corning Toray Silicone Co., Ltd., Tokyo, Japan

[21] Appl. No.: 672,385

[22] Filed: May 29, 1996

[30] Foreign Application Priority Data

May 31, 1995 [JP] Japan ................................. 7-157176

[51] Int. Cl.$^6$ .................................. C07F 7/08; C07F 7/10
[52] U.S. Cl. ....................... 556/413; 556/410; 556/449; 556/451; 549/215
[58] Field of Search .................. 556/413, 410, 556/449, 451; 549/215

[56] References Cited

U.S. PATENT DOCUMENTS

| | | | |
|---|---|---|---|
| 5,097,054 | 3/1992 | Yamamoto et al. | 556/451 |
| 5,232,959 | 8/1993 | Togashi et al. | 556/451 X |
| 5,443,633 | 8/1995 | Hirsbrunner et al. | 556/451 X |
| 5,446,185 | 8/1995 | Cobb et al. | 556/451 |
| 5,486,635 | 1/1996 | Okawa | 556/451 X |
| 5,493,040 | 2/1996 | Cobb et al. | 556/451 |

FOREIGN PATENT DOCUMENTS

| | | |
|---|---|---|
| 80779 | 3/1994 | Japan . |
| 80783 | 3/1994 | Japan . |

OTHER PUBLICATIONS

Polymer Preprints, Japan, vol. 42, pp. 486, 487, 1496, (1993).

*Primary Examiner*—Paul F. Shaver
*Attorney, Agent, or Firm*—Alexander Weitz

[57] ABSTRACT

There is disclosed an organosilicon compound which contains a silicon-bonded functional group at each molecular chain terminal as well as a terminal -SiH group on a side chain branching from the main chain, said functional group being selected from amino-functional organic groups, epoxy-functional organic groups, hydroxyl group or a group obtained by substituting active hydrogen in the preceding groups with triorganosilyl group.

18 Claims, No Drawings

ORGANOSILICON COMPOUNDS AND METHOD FOR THE PREPARATION THEREOF

DETAILED DESCRIPTION OF THE INVENTION

1. Field of the Invention

This invention relates to novel organosilicon compounds and a method for their preparation. More particularly, this invention relates to novel organosilicon compounds that carry a silicon-bonded organofunctional group at both molecular chain terminals while bearing SiH in terminal position on a side chain branching from the main chain. The invention also relates to a method for the preparation of the described novel organosilicon compounds.

2. Background of the Invention

Organofunctionalized organopolysiloxanes are used to impart the desirable properties characteristic of organosiloxanes to conventional organic resins, such as water repellency, release properties, waterproofness, lubricity, weathering resistance, heat resistance, selective gas permeability, inter alia. There have recently been a number of reports on heteropolyfunctional silicone compounds that are regarded as well-adapted for the modification or improvement of organic resins. When silicone compounds of this type are used to modify organic resins, the functional groups remaining in the resulting silicone-modified organic resin can be exploited for subsequent crosslinking and curing reactions. For example, Japanese Patent Application Laid Open Number Hei 6-80779 discloses a difunctional silicone compound that contains silicon-bonded hydrogen and the dicarboxylic anhydride group in the same molecule. In this case, the dicarboxylic anhydride group can be used for the modification of polyimide resin and the Si-bonded hydrogen remaining in the modified resin is available for crosslinking reactions. Japanese Patent Application Laid Open Number Hei 6-80783 discloses a silicone-modified polyimide resin that possesses a plurality of silicon-bonded hydrogen at the terminals of the polymer main chain.

There are also disclosed in Polymer Preprints, Japan, Volume 42, pp. 486, 487, 1496 (1993) a silicone compound that can introduce SiH into the polymer main chain and a silicone compound bearing both SiH and polycarboxylic anhydride moieties. The latter compound is synthesized by Grignard and Dieis-Alder reactions.

With respect to the aforementioned heteropolyfunctional silicone compounds, however, the SiH is introduced in each case at the terminals of the polymer main chain, which necessarily restricts the SiH content to a very limited range. While introduction of SiH into the polymer main chain is desirable in order to broaden the range from which the SiH content can be selected, the synthesis of the corresponding silicone compounds has required the use of organometals and has proceeded through a multistep process that includes a by-product-rich Grignard reaction. As a result, there is a need for novel heteropolyfunctional silicone compounds that are well-suited for the modification of organic resins. The introduction of a simple method for the preparation of these compounds is also desired.

SUMMARY OF THE INVENTION

Therefore, an object of the present invention is to provide novel heteropolyfunctional silicone compounds that bear organofunctional groups at both terminals and carry silicon-bonded hydrogen in the main chain. Another object of the present invention is to provide a method for the preparation of these novel heteropolyfunctional silicone compounds.

The present invention relates to organosilicon compounds with the general formula

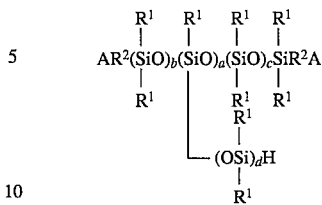

wherein each $R^1$ is independently selected from $C_1$ to $C_{20}$ monovalent hydrocarbon groups that are free of aliphatic unsaturation; $R^2$ represents a $C_1$ to $C_{20}$ divalent organic group; A is a group selected from amino-functional organic groups, epoxy-functional organic groups, hydroxyl group or a group obtained by substituting active hydrogen in the preceding groups with triorganosilyl; a is an integer from 1 to 20; b is an integer from 1 to 20; c is an integer from 0 to 20; and d is an integer from 1 to 20.

The invention also relates to a method for the preparation of the above organosilicon compounds wherein said method is characterized by the addition reaction, in the presence of a platinum catalyst, between (A) an organosilicon compound with the general formula

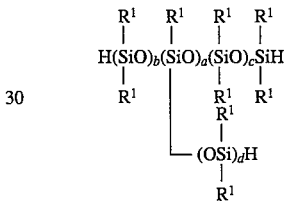

wherein each $R^1$ is independently selected from $C_1$ to $C_{20}$ monovalent hydrocarbon groups that are free of aliphatic unsaturation, a is an integer from 1 to 20, b is an integer from to 20, c is an integer from 0 to 20, and d is an integer from 1 to 20 and (B) an aliphatically unsaturated organic compound containing a group selected from amino-functional organic groups, epoxy-functional organic groups, hydroxyl group or an aliphatically unsaturated organic compound as obtained by substituting active hydrogen in the aforesaid groups with triorganosilyl.

The present invention has been disclosed in Japanese Patent Application Number Hei 07/157176, the full disclosure of which is hereby incorporated by reference.

DETAILED DESCRIPTION OF THE INVENTION

Organosilicon compounds according to the present invention are defined by the formula

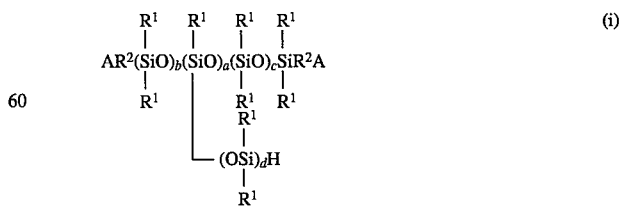

(i)

Each $R^1$ in this formula is independently selected from $C_1$ to $C_{20}$ monovalent hydrocarbon groups that are free of aliphatic unsaturation. $R^1$ is specifically exemplified by alkyl groups such as methyl, ethyl, propyl, butyl, and so forth; aryl groups such as phenyl, tolyl, xylyl, and so forth; and substituted alkyl groups such as chloromethyl, perfluoromethyl, and so forth. Considerations such as cost and availability of starting materials make it desirable for methyl to constitute at least 80% of the subject monovalent hydrocarbon groups. $R^2$ represents $C_1$ to $C_{20}$ divalent organic groups and is specifically, but nonexhaustively, exemplified by alkylene groups such as methylene, ethylene, propylene, butylene, and so forth, and by arylene groups such as phenylene, tolylene, xylylene, and so forth. A is a group selected from amino-functional organic groups, epoxy-functional organic groups, hydroxyl group or a group obtained by substituting at least one active hydrogen in any one of the preceding groups with triorganosilyl. The following groups are examples of organofunctional groups in which group A is bonded with $R^2$ $H_2NC_3H_6-$
$CH_3NHC_3H_6-$
$CH_3NHC_4H_8-$
$(CH_3)_3SiNHC_3H_6-$

$(CH_3)_3SiOC_2H_4OC_3H_6-$
$H_2NC_2H_4NHC_3H_6-$

The subscripts a and b in the preceding general formula (i) are both integers from 1 to 20 and preferably from 1 to 5. The subscript c is an integer from 0 to 20 and preferably from 0 to 3, and the subscript d is an integer from 1 to 20 and preferably from 1 to 5.

The subject organosilicon compounds of formula (i) are specifically exemplified by the following

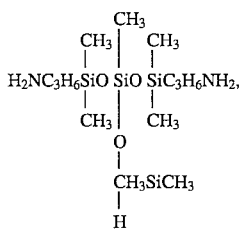

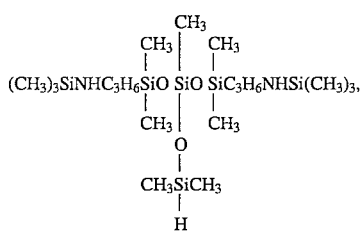

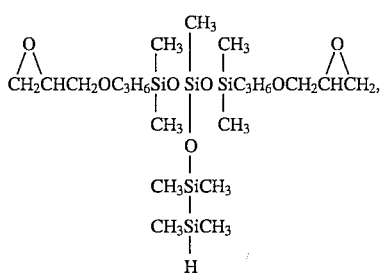

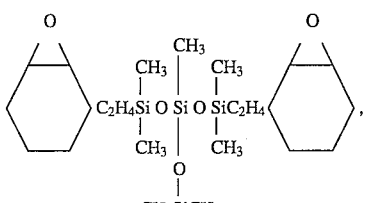

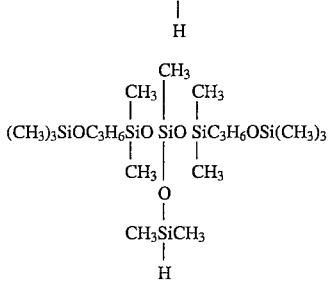

and

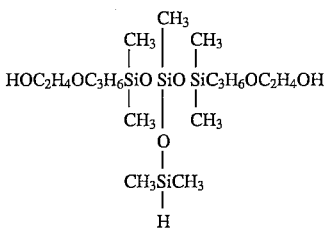

The method according to the present invention for the preparation of the above-described organosilicon compounds according to formula (i) will now be considered.

The organosilicon compound (A) used by the preparative method according to the present invention is defined by the following formula.

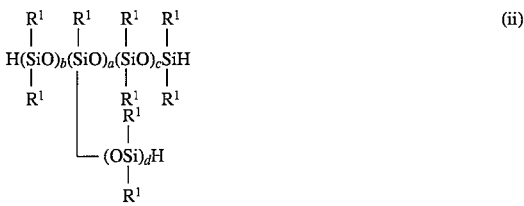 (ii)

wherein $R^1$, a, b and c are as defined above. The organosilicon compound (A) is specifically exemplified by compounds with the following formulas

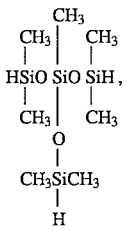

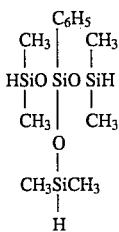

and

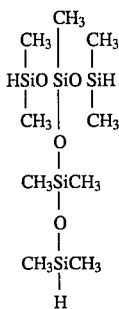

The compound (B) used in the preparative method according to the present invention is an aliphatically unsaturated organic compound containing a group selected from amino-functional organic groups, epoxy-functional organic groups, hydroxyl group or an aliphatically unsaturated organic compound obtained by substituting triorganosilyl for active hydrogen in the aforesaid groups. Compound (B) is specifically exemplified by the following compounds
$H_2NCH_2CH=CH_2$,
$CH_3NHCH_2CH=CH_2$,
$CH_3NHC_2H_4CH=CH_2$,
$(CH_3)_3SiNHCH_2CH=CH_2$,

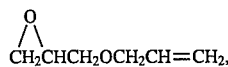

$(CH_3)_3SiOCH_2CH=CH_2$,
$(CH_3)_3SiOC_2H_4OCH_2CH=CH_2$ and
$H_2NC_2H_4NHCH_2CH=CH_2$ The organosilicon compound (A) and compound (B) are preferably used in the preparative method according to the present invention in quantities that yield a molar ratio in the range defined by the following equation:

$$2 \leq \frac{\text{number of moles of compound (B)}}{\text{number of moles of organosilicon compound (A)}} \leq 2.5$$

When a compound B/organosilicon compound (A) molar ratio of less than about 2 is used, the adduct of only a single molecule of compound (B) to organosilicon compound (A) is obtained. When this molar ratio exceeds about 2.5, large amounts of adduct will be produced in which 3 molecules of compound (B) have added to the organosilicon compound (A). Either case results in a reduced yield of the desired organosilicon compound according to the formula (i).

The catalyst used for the addition reaction between organosilicon compound (A) and compound (B) comprises those catalysts generally used to promote hydrosilylation reactions.

The catalyst is specifically, but nonexhaustively, exemplified by platinum catalysts such as chloroplatinic acid, alcohol solutions of chloroplatinic acid, platinum/olefin complexes, platinum/vinylsiloxane complexes, and the like, as well as by rhodium catalysts such as Wilkinson's complex, rhodium/carbonyl complexes, the like. The catalyst should be used in this addition reaction at a level of about 1 to 100 weight parts as platinum atoms (preferably at from 1 to 50 weight parts as platinum atoms) for each 1,000,000 weight parts of the total amount of organosilicon compound (A) and compound (B). The addition reaction may not develop at less than 1 weight part, while the addition reaction is not accelerated in proportion to the amount used at above about 100 weight parts and the use of large amounts of these expensive catalysts is uneconomical.

The temperature of the addition reaction is not crucial, but will generally fall in the range from about 50° C. to 250° C. and preferably falls in the range from 50° C. to 200° C. Reaction temperatures below about 50° C. result in a slower reaction rate, and hence a diminished productivity. Reaction temperatures in excess of about 250° C. cause the occurrence of undesirable secondary reactions, such as, the production of adduct in which 3 molecules of compound (B) have added to the organosilicon compound (A).

Organic solvent may be used on an optional basis in the addition reaction under consideration as long as the objects of the invention remain unimpaired. Operable organic solvents are exemplified by toluene, xylene, hexane, heptane, tetrahydrofuran, 1,4 - dioxane, and the like.

After completion of the addition reaction, the organosilicon product can be recovered by distillation from the reaction mixture. Alternatively, the product may be obtained by eliminating the low-boiling components from the reaction mixture by distillation at reduced pressure.

Organosilicon compounds according to the present invention are useful as modifiers or improvers for various types of organic resins. Organic resins modified or improved by the subject organosilicon compounds exhibit such properties as a highly durable adherence for a variety of substrates, an improved moisture resistance, and so forth.

EXAMPLES

The invention will be more specifically explained in the following with reference to working examples.

Example 1

An organosilicon compound (164.1 g) with the following formula was introduced under nitrogen into a four-neck flask equipped with stirrer, reflux condenser, addition funnel, and thermometer

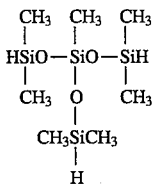

The flask was stirred and heated, and when the liquid temperature reached 90° C., 14 mg of chloroplatinic acid/1,3-divinyl-1,1,3,3-tetramethyldisiloxane complex (platinum atom concentration=5 weight%) was introduced. N-trimethylsilylallylamine (175.2 g) was then added dropwise over a period of 3.5 hours, during which time the reaction temperature rose to 175° C. During this addition, more of the above described platinum-vinylsiloxane complex was added as appropriate to ultimately bring its total to 49 mg. Stirring was continued for 30 minutes after the completion of addition and this was followed by cooling to room temperature.

Anhydrous methanol (44.9 g) was added dropwise over a period of 23 minutes, during which time the reaction temperature varied from 27° C. to 48° C. After the completion, of addition stirring was continued for 46 minutes at 43° C to 48° C. After cooling to room temperature, a Vigreux fractionation column was installed and distillation was carried out to yield 147.9 g (yield=63%) of an organosilicon compound with the following formula as the fraction at 168° C./10 mmHg–186° C./10 mmHg.

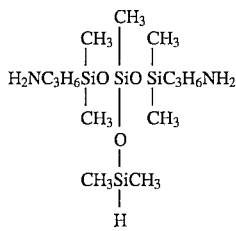

Example 2

An organosilicon compound (37.6 g) with the following formula was introduced under nitrogen into a four-neck flask equipped with stirrer, reflux condenser, addition funnel, and thermometer

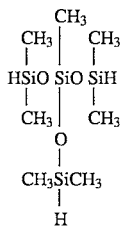

The flask was stirred and heated, and when the liquid temperature reached 110° C., 14 mg of chloroplatinic acid/1,3-divinyl-1,1,3,3-tetramethyldisiloxane complex (platinum atom concentration=5 weight%) was introduced. Allyl glycidyl (32.0g) ether was then added dropwise over a period of 1.1 hours, during which time the reaction temperature rose to 203° C. Stirring was continued for 43 minutes after the completion of addition and this was followed by cooling to room temperature. A Vigreux fractionation column was then installed and distillation was carried out to yield 49.4 g (yield=71%) organosilicon compound with the following formula as the fraction at 170° C./2 mmHg–178° C./2 mmHg

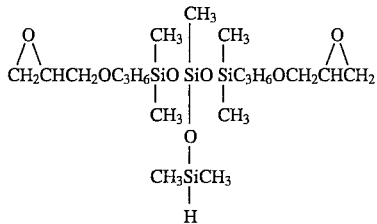

Example 3

An organosilicon compound (26.9 g) with the following formula was introduced under nitrogen into a four-neck flask equipped with stirrer, reflux condenser, addition funnel, and thermometer

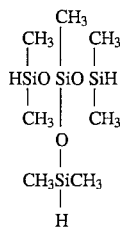

The flask was stirred and heated, and when the liquid temperature reached 95° C., 14 mg of chloroplatinic acid/1,3-divinyl-1,1,3,3-tetramethyldisiloxane complex (platinum atom concentration=5 weight%) was introduced. Trimethylsilyl allyl ether (26.1g) was then added dropwise over a period of 1.7 hours, during which time the reaction temperature rose to 167° C. Stirring was continued for 55 minutes after the completion of addition and this was followed by cooling to room temperature. A Vigreux fractionation column was then installed and distillation was carried out to yield 39.7 g (yield=75%) organosilicon compound with the following formula as the fraction at 143° C./2 mmHg–146° C./2 mmHg

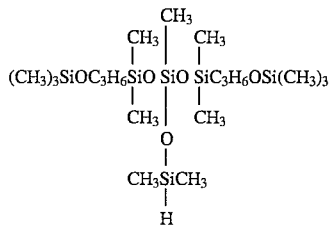

Application Example

While operating under nitrogen, 6.3 g of pyromellitic dianhydride and 34.8 g of a mixture of N,N-dimethylacetamide and xylene (mixing ratio=95:5 by weight) were introduced into a flask equipped with stirrer, addition funnel, and thermometer and were stirred. The addition funnel was charged with 11.1 g of the organosilicon compound prepared in Example 1 and 34.8 g of a mixture of N,N-dimethylacetamide and xylene (mixing ratio=9:5 by weight). This diaminosiloxane solution was added dropwise from the addition funnel over a period of 29 minutes, during which time the reaction temperature varied from 29° C. to 37° C. This was followed by stirring for 3.5 hours at 37° C. to 26° C. A Dean-Stark receiver was installed and an azeotropic dehydration was run for 8 minutes at 144° C. to 146° C. Cooling to room temperature and filtration yielded 77.3 g of a polyimide solution.

When the infrared absorption spectrum of this solution was measured, the SiH signal at 2130 cm$^{-1}$ and the imide group signals at 1780 cm$^{-1}$ and 1720 cm$^{-1}$ were observed. When this polyimide solution was held for 6 months at room temperature, it remained a homogeneous solution and did not manifest such changes as gel production, precipitate development or viscosity increase.

This polyimide solution was coated on a silicon wafer, glass plate, and aluminum sheet, and in each case a polyimide film was produced by curing for 3 hours in a 160° C. oven. A pressure cooker test was then run for 20 hours at 121° C./100% RH (relative humidity). When a crosshatch adhesion test was conducted on each of these polyimide films, it was found that the polyimide resins adhered well to the various substrates.

That which is claimed is:

1. An organosilicon compound having a formula selected from the group consisting of

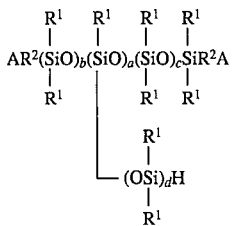

and

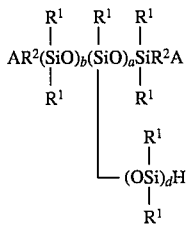

in which each $R^1$ is independently selected from $C_1$ to $C_{20}$ monovalent hydrocarbon radicals, each $R^2$ is selected from $C_1$ to $C_{20}$ divalent organic groups, A is selected from the group consisting of amino-functional organic groups, epoxy-functional organic groups, hydroxyl group and a group obtained by substituting an active hydrogen in one of the preceding groups with triorganosilyl group, a is an integer from 1 to 20, b is an integer from 1 to 20, c is an integer from 1 to 20, and d is an integer from 1 to 20.

2. The organosilicon compound according to claim 1, wherein $R^1$ is methyl.

3. The organosilicon compound according to claim 1 having the formula

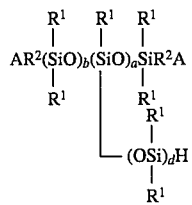

in which each $R^1$ is independently selected from $C_1$ to $C_{20}$ monovalent hydrocarbon radicals, each $R^2$ is selected from $C_1$ to $C_{20}$ divalent organic groups, A is selected from the group consisting of amino-functional organic groups, epoxy-functional organic groups, hydroxyl group and a group obtained by substituting an active hydrogen in one of the preceding groups with triorganosilyl group and a=b=d=1.

4. The organosilicon compound according to claim 3, wherein $R^1$ is methyl.

5. The organosilicon compound according to claim 1, wherein $-R^2A$ has a formula selected from the group consisting of
$H_2NC_3H_6-$,
$CH_3NHC_3H_6-$,
$CH_3NHC_4H_8-$,
$(CH_3)_3SiNHC_3H_6-$,

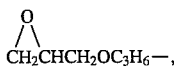

$(CH_3)_3SiOC_3H_6-$,
$(CH_3)_3SiOC_2H_4OC_3H_6-$ and
$H_2NC_2H_4NHC_3H_6-$.

6. The organosilicon compound according to claim 5, wherein $R^1$ is methyl.

7. The organosilicon compound according to claim 3, wherein $-R^3A$ has a formula selected from the group consisting of
$H_2NC_3H_6-$,
$CH_3NHC_3H_6-$,
$CH_3NHC_4H_8-$,
$(CH_3)_3SiNHC_3H_6-$,

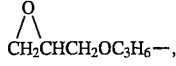

$(CH_3)_3SiOC_3H_6-$,
$(CH_3)_3SiOC_2H_4OC_3H_6-$ and
$H_2NC_2H_4NHC_3H_6-$.

8. The organosilicon compound according to claim 7, wherein $R^1$ is methyl.

9. The organosilicon compound according to claim 1, wherein A is selected from the group consisting of epoxycyclohexyl, glycidoxy and $-N(H)Si(CH_3)_3$.

10. The organosilicon compound according to claim 9, wherein $R^1$ is methyl.

11. A method for preparing an organosilicon compound comprising reacting, in the presence of a platinum catalyst, (A) an organosilicon compound having a formula selected from the group consisting of

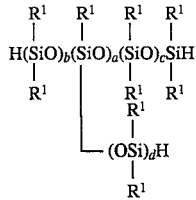

and

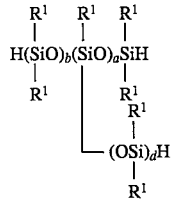

in which each $R^1$ is independently selected from $C_1$ to $C_{20}$ monovalent hydrocarbon radicals, a is an integer from 1 to 20, b is an integer from 1 to 20, c is an integer from 1 to 20, and d is an integer from 1 to 20; and (B) an aliphatically unsaturated organic compound containing a functional group selected from the group consisting of amino-functional organic groups, epoxy-functional organic groups, hydroxyl group and a group obtained by substituting active hydrogen in the aforesaid organofunctional groups with triorganosilyl.

12. The method according to claim 10, wherein $R^1$ is methyl.

13. The method according to claim 10, wherein said aliphatically unsaturated organic compound (B) has a formula selected from the group consisting of
H$_2$NCH$_2$CH=CH$_2$,
CH$_3$NHCH$_2$CH=CH$_2$,
CH$_3$NHC$_2$H$_4$CH=CH$_2$,
(CH$_3$)$_3$SiNHCH$_2$CH=CH$_2$,

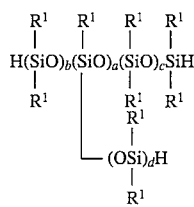
CH$_2$CHCH$_2$OCH$_2$CH=CH$_2$, (CH$_3$)$_3$SiOCH$_2$CH=CH$_2$,
(CH$_3$)$_3$SiOC$_2$H$_4$OCH$_2$CH=CH$_2$ and
H$_2$NC$_2$H$_4$NHCH$_2$CH=CH$_2$.

14. The method according to claim 13, wherein R$^1$ is methyl.

15. An organosilicon compound prepared by reacting, in the presence of a platinum catalyst, (A) an organosilicon compound having a formula selected from the group consisting of

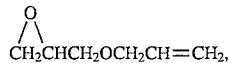

and

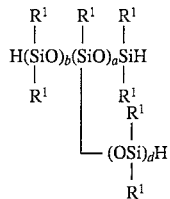

in which each R$^1$ is independently selected from C$_1$ to C$_{20}$ monovalent hydrocarbon radicals, a is an integer from 1 to 20, b is an integer from 1 to 20, c is an integer from 1 to 20, and d is an integer from 1 to 20; and (B) an aliphatically unsaturated organic compound containing a functional group selected from the group consisting of amino-functional organic groups, epoxy-functional organic groups, hydroxyl group and a group obtained by substituting active hydrogen in the aforesaid organofunctional groups with triorganosilyl, wherein the molar ratio of said aliphatically unsaturated organic compound (B) to said organosilicon compound (A) is in the range of 2 to 2.5.

16. The organosilicon compound according to claim 15, wherein R$^1$ is methyl.

17. The organosilicon compound according to claim 15, wherein said aliphatically unsaturated organic compound (B) has a formula selected from the group consisting of
H$_2$NCH$_2$CH=CH$_2$,
CH$_3$NHCH$_2$CH=CH$_2$,
CH$_3$NHC$_2$H$_4$CH=CH$_2$,
(CH$_3$)$_3$SiNHCH$_2$CH=CH$_2$,

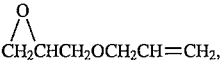
CH$_2$CHCH$_2$OCH$_2$CH=CH$_2$, (CH$_3$)$_3$SiOCH$_2$CH=CH$_2$,
(CH$_3$)$_3$SiOC$_2$H$_4$CH$_2$CH=CH$_2$ and
H$_2$NC$_2$H$_4$NHCH$_2$CH=CH$_2$.

18. The organosilicon compound according to claim 17, wherein R$^1$ is methyl.

* * * * *